US00PP21088P2

(12) United States Plant Patent

Klemm et al.

(10) Patent No.: US PP21,088 P2

(45) Date of Patent: Jun. 22, 2010

(54) *OSTEOSPERMUM* PLANT NAMED 'KLEOE08149'

(50) Latin Name: *Osteospermum ecklonis*
Varietal Denomination: KLEOE08149

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,406

(22) Filed: Mar. 24, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Susan B McCormick Ewoldt
(74) *Attorney, Agent, or Firm*—Jondle & Associates, P.C.

(57) ABSTRACT

An *Osteospermum* cultivar named 'KLEOE08149' particularly distinguished by deep greyed-orange inflorescences, good branching, and a compact and stable growth habit, is disclosed.

1 Drawing Sheet

Genus and species: *Osteospermum ecklonis.*
Variety denomination: 'KLEOE08149'.

BACKGROUND OF THE NEW PLANT

The present invention comprises a new and distinct cultivar of *Osteospermum*, botanically known as *Osteospermum ecklonis*, and hereinafter referred to by the cultivar name 'KLEOE08149'. The new cultivar originated from a hybridization made in July 2005 in Stuttgart, Germany. The female parent was an un-named *Osteospermum* plant (unpatented), while the male parent was 'FlowerPower Sunrise' (unpatented) *Osteospermum* plant, with light yellow inflorescences. The seeds produced by the hybridization were sown in Spring 2006. A single plant selection was chosen for further evaluation and for asexual propagation in Spring 2006.

The new cultivar was created in 2005 in Stuttgart, Germany, and has been asexually reproduced repeatedly by vegetative cuttings in Stuttgart, Germany over a two and one-half year period. The present invention has been found to retain its distinctive characteristics through successive asexual propagations.

Plant Breeder's Rights for this cultivar have been applied for in Switzerland on Aug. 5, 2008. 'KLEOE08149' has not been made publicly available more than one year prior to the filing date of this application.

SUMMARY OF THE INVENTION

The following are the most outstanding and distinguishing characteristics of the new cultivar when grown under normal horticultural practices in Stuttgart, Germany.

1. Deep greyed-orange inflorescences;
2. Good branching; and
3. A compact and stable growth habit.

DESCRIPTION OF THE PHOTOGRAPH

This new *Osteospermum* plant is illustrated by the accompanying photograph which shows blooms, buds, and foliage of the plant; the colors shown are as true as can be reasonably obtained by conventional photographic procedures.

The photograph is of a plant about 4 to 5 months old taken in Summer 2008 in a field in Stuttgart, Germany under conditions which approximate those generally used in commercial practice.

DESCRIPTION OF THE NEW CULTIVAR

The following detailed descriptions set forth the distinctive characteristics of 'KLEOE08149'. The data which define these characteristics were collected from asexual reproductions carried out in Stuttgart, Germany. The plant history was taken on plants about 4 to 5 months old, grown in the field. The plants were pinched once at 12 weeks. Color readings were taken under natural light. Color references are primarily to The R.H.S. Colour Chart of The Royal Horticultural Society of London (RHS) (2001).

DESCRIPTION OF THE NEW PLANT

Classification:
- *Family.*—Asteraceae.
- *Botanical name.*—*Osteospermum ecklonis.*
- *Common name.*—African daisy.

Parentage:
- *Female parent.*—The female parent was an un-named *Osteospermum* plant (unpatented).
- *Male parent*—The male parent was 'FlowerPower Sunrise' (unpatented) *Osteospermum* plant.

Plant:
- *Growth and branching habit.*—Upright.
- *Height (from top of soil, including inflorescence).*—30.0 cm.
- *Width (including inflorescences).*—35.0 cm.
- *Propagation.*—Cuttings.
- *Time to produce a finished flowering plant.*—10 weeks.
- *Outdoor plant performance.*—Continuous flowering, compact growth.
- *Time to initiate and develop roots.*—4 weeks.
- *Root description.*—Freely rooting.

Leaves:
- *Arrangement.*—Arranged in a whorl.

*Shape.*—Dentiform.
*Apex.*—Obtuse.
*Base.*—Acute.
*Margin.*—Serrated, medium indentations for immature leaves and deep indentations for mature leaves.
*Texture.*—Leathery (mature leaf) and rough (immature leaf).
*Immature leaf.*—Color (both upper and lower surfaces): RHS 146B.
*Mature leaf:.*—Color: Upper surface: RHS 147A. Lower surface: RHS 147B.
*Length.*—6.0 cm (mature leaf) and 3.0 cm (immature leaf).
*Width.*—2.0 cm (mature leaf) and 1.5 cm (immature leaf).
*Petioles.*—Absent.
*Venation pattern.*—Pinnate.

Stems:
*Total number of branches.*—6 to 7.
*Length.*—30.0 cm.
*Diameter.*—0.2 cm.
*Internode length.*—3.0 cm.
*Color.*—RHS 146B and RHS 146C.
*Texture.*—Rough.
*Anthocyanin.*—Absent.

Inflorescence buds:
*Shape.*—Obovate.
*Diameter.*—1.5 cm.
*Length.*—2.5 cm.
*Color* (*at tight bud just before the ray florets unfold*).—RHS 146B and RHS 146C.

Inflorescence:
*Type.*—Single.
*Blooming habit.*—Plants flower continuously from Spring to Fall given the proper growing conditions.
*Quantity of inflorescences per plant.*—About 30.
*Lastingness of the inflorescences on the plant.*—7 to 10 days.
*Fragrance.*—Absent.
*Inflorescence diameter.*—6.0 cm to 7.0 cm.
*Inflorescence depth.*—Variable throughout flower development.
*Disc diameter.*—6.0 cm to 7.0 cm.

Disc floret: Absent.

Ray floret:
*Quantity per inflorescence.*—20.
*Shape.*—Lanceolate.
*Color.*—Upper surface: RHS 163A fading to RHS 182B (ring around the disc). Lower surface: RHS 185A fading to RHS 164B.
*Length* (*including peduncle*).—3.5 cm.
*Width.*—0.6 cm.
*Apex.*—Obtuse.
*Base.*—Acute.
*Margin.*—Entire.
*Texture.*—Smooth.
*Peduncle.*—Length: 2.3 cm. Diameter: 0.1 cm. Texture: Rough. Color: RHS 144A.

Phyllaries:
*Arrangement.*—Single.
*Observed quantity per plant.*—20.
*Shape.*—Lanceolate.
*Color.*—Upper surface: RHS 144A. Lower surface: RHS 144B.
*Length.*—2.0 cm.
*Width:* 0.2 *cm.*
*Apex.*—Acute.
*Base.*—Acute.
*Margin.*—Entire.
*Texture.*—Rough.

Reproductive organs:
*Androecium.*—Present. Stamens: Stamen quantity: Too numerous to quantify. Stamen shape: Filamentous. Stamen color: RHS 155A and RHS 155B. Filament length: 0.3 cm. Filament diameter: 0.0005 cm. Anther: Shape: Elliptic. Color: RHS 200A and RHS 200B. Length: 0.25 cm. Diameter: 0.005 cm. Pollen: Pollen color: RHS 17B and RHS 17C. Pollen amount: Sparse
*Gynoecium.*—Pistils: Number: Greater than 20. Pistil length: 1.7 cm. Diameter: 0.001 cm. Stigma: Stigma color: RHS 202A. Shape: Ovate. Length: 0.2 cm. Diameter: 0.001 cm. Style: Style color: RHS 186A fading to RHS 188A. Style length: 0.5 cm. Diameter: 0.001 cm. Shape: Filamentous.

Fruit and seed set: None observed.

Disease and insect resistance: No particular disease or insect resistance observed.

COMPARISON WITH PARENTAL AND COMMERCIAL CULTIVARS

'KLEOE08149' differs from the male parent 'FlowerPower Sunrise' (unpatented) in that 'KLEOE08149' has deep greyed-orange inflorescences and a compact and upright growth habit, while 'FlowerPower Sunrise' has lighter colored inflorescences, less branching, and a more spreading growth habit.

'KLEOE08149' differs from commercial cultivar 'KLEOE06150' (U.S. plant application Ser. No. 12/005,906, now abandoned) in that 'KLEOE08149' has deep greyed-orange inflorescences and a compact growth habit, while 'KLEOE06150' (U.S. plant application Ser. No. 12/055,096) has lighter colored inflorescences and a very compact growth habit.

I claim:

1. A new and distinct cultivar of *Osteospermum* plant named 'KLEOE08149' as shown and described herein.

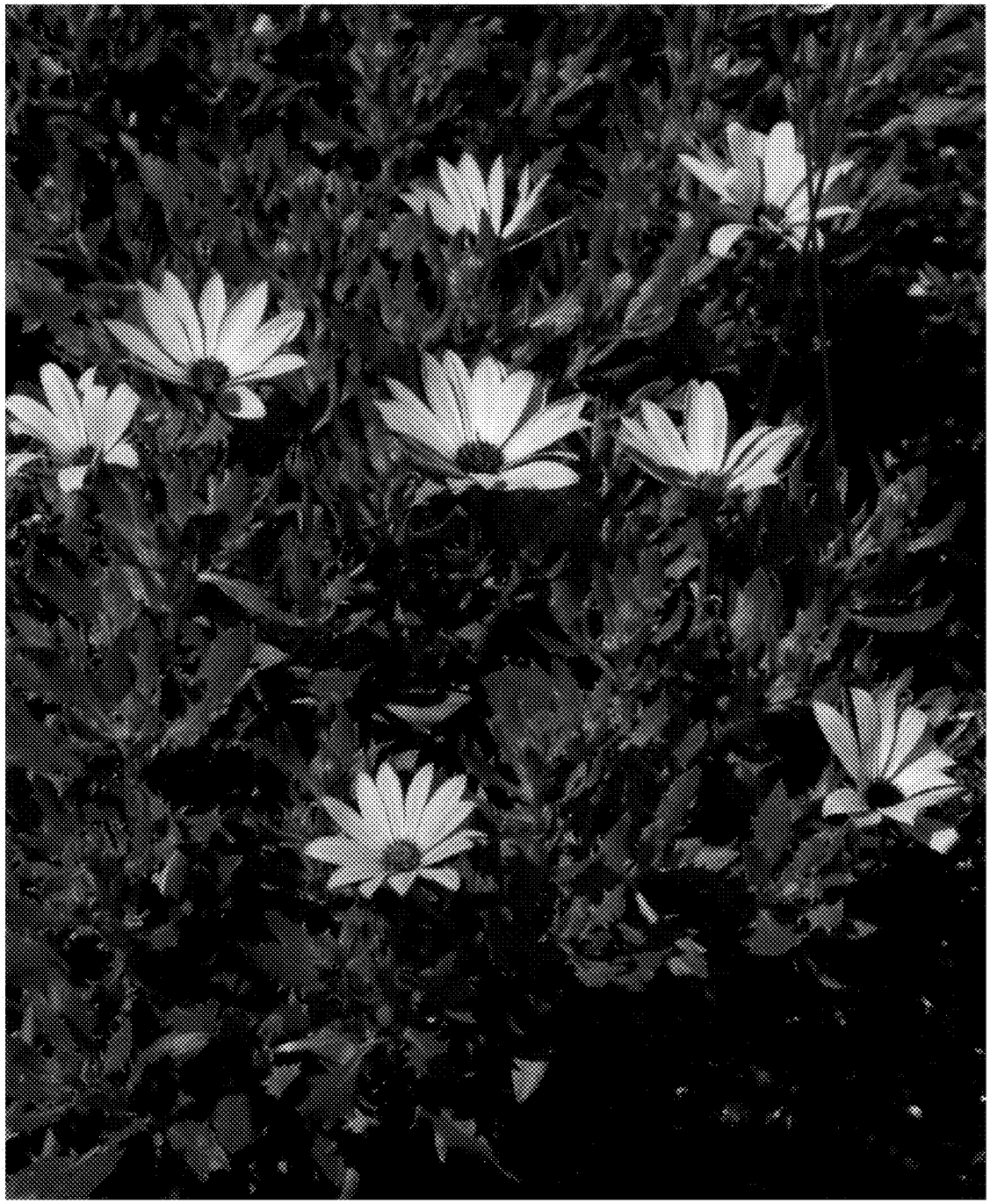

* * * * *